United States Patent [19]

Virrion et al.

[11] 4,185,113

[45] Jan. 22, 1980

[54] STABILIZED METAL SALTS OF ETHYLENE BIS DITHIOCARBAMIC ACID

[75] Inventors: Aimé Virrion; Claude Franson, both of Marseilles, France

[73] Assignee: Roussel UCLAF, Paris, France

[21] Appl. No.: 940,275

[22] Filed: Sep. 7, 1978

Related U.S. Application Data

[63] Continuation of Ser. No. 775,623, Mar. 8, 1977, abandoned.

[30] Foreign Application Priority Data

Mar. 10, 1976 [FR] France .................. 76 06814

[51] Int. Cl.$^2$ .................. A01N 9/12; A01N 9/20; A01N 9/24; C07C 155/00
[52] U.S. Cl. .................. 424/286; 260/429 K; 260/429.9; 260/513.5; 424/333
[58] Field of Search .................. 424/286, 333; 260/513.5, 429, 429.9

[56] References Cited

U.S. PATENT DOCUMENTS

| 3,173,832 | 3/1965 | Harris | 424/286 |
| 3,294,829 | 12/1966 | Lehmann et al. | 424/286 |
| 3,699,231 | 10/1972 | Werlein et al. | 424/286 |
| 3,856,851 | 12/1974 | Buckman et al. | 424/286 |

FOREIGN PATENT DOCUMENTS

| 1344342 | 10/1963 | France . | |
| 1374622 | 8/1964 | France | 424/286 |
| 1476610 | 4/1967 | France | 424/286 |
| 2096961 | 3/1972 | France . | |
| 2096963 | 3/1972 | France . | |

*Primary Examiner*—Douglas W. Robinson
*Attorney, Agent, or Firm*—Hammond & Littell

[57] ABSTRACT

Compositions containing stabilized metal salts of ethylene bis dithiocarbamic acid with cinnamic aldehyde or a compound resulting from the conversion of cinnamic aldehyde which are useful as fungicides and to a process of stabilizing said metal salts.

9 Claims, No Drawings

STABILIZED METAL SALTS OF ETHYLENE BIS DITHIOCARBAMIC ACID

PRIOR APPLICATION

This application is a continuation of our copending, commonly assigned U.S. patent application Ser. No. 775,623 filed Mar. 8, 1977, now abandoned.

STATE OF THE ART

Metal salts of ethylene bis dithiocarbamic acid are known to have fungicidal properties and manganese ethylene bis dithiocarbamate also known as maneb and zinc ethylene bis dithiocarbamate also known as zineb have been used for a long time on a large scale as agricultural fungicides. Maneb and zineb are usually prepared in an aqueous media by reaction of a water soluble salt of ethylene bis dithiocarbamic acid such as the ammonium, calcium or sodium salt with a water soluble zinc or manganese salt such as its sulfate. After precipitation and drying, the resulting salts are then combined with the necessary adjuvants to obtain a fungicidal composition.

It is also known that maneb and zineb are not stable compounds and they are easily degraded by the action of heat, oxygen and humidity. This instability makes it difficult for industrial preparation, particularly in the drying step. The drying normally is effected without particular precautions since at normal pressure and a temperature on the order of 80° to 110° C., noting, in general, a profound alteration of the zinc and manganese salts which is manifested by a change in color, (for example, the color of maneb goes from yellow to maroon to black) and by a formation of decomposition products with a disagreeable odor. This alteration may be pushed to end in a spontaneous inflammation in the case of maneb which inflammation probably is tied to the liberation of carbon sulfide.

Also when drying is conducted under more gentle conditions such as under reduced pressure at lower temperatures, which is more onerous, the active principle, during the ultimate storage in the form of salts or compositions containing the salts, generally undergo an especially important degradation if the storage is under hot and humid conditions. This degradation is manifested by an alteration of color, formation of compounds having a disagreeable odor and by an important reduction in titer (lessening of analytical titer in $CS_2$) that as a consequence causes a lessening of fungicidal activity. Besides, the decomposition processes, which are complex, result in the formation of diverse degradation products which, in an important quantity, are able to provoke phytotoxicity to the plants and constitute undesirable residues for eating.

Prior art, attempting to avoid these inconveniences, led to the use of various stabilizers. French Pat. No. 1,344,342 teaches the use of paraformaldehyde, French Pat. No. 1,374,622 teaches the use of o-, p- or m-phenylene diamine and French Pat. No. 1,476,610 teaches the use of 1,8- 3,6-diendomethylene-1,3,6,8-tetraazacyclodecane as a stabilizer but none have been completely satisfactory.

OBJECTS OF THE INVENTION

It is an object of the invention to provide stabilized metal salts of ethylene bis dithiocarbamic acid.

It is another object of the invention to provide a novel method of stabilizing compositions containing metal salts of ethylene bis dithiocarbamic acid.

These and other objects and advantages of the invention will become obvious from the following detailed description.

THE INVENTION

The stabilized salts of the invention are comprised of at least one metal salt of ethylene bis dithiocarbamic acid stabilized with a sufficient quantity of cinnamic aldehyde or of a compound resulting from the conversion of cinnamic aldehyde, formed particularly in the presence of metal salts of ethylene bis dithiocarbamic acid during the period of stabilization. The preferred metal salts are manganese and zinc salts.

To ensure a good stabilization of a metal salt of ethylene bis dithiocarbamic acid, especially maneb or zineb and compositions containing the said salts, the preferred amount of cinnamic aldehyde is 0.1 to 10% by weight based on the weight of the stabilized salt or 0.1 to 20% by weight based on the weight of the stabilized fungicidal composition. However, higher or lower ratios are within the scope of the invention although the above ranges are the most practical ranges.

The stabilized fungicidal compositions of the invention may be in the form of powders, wettable powders, granules, suspensions, emulsions or solutions containing the said salt and the stabilizer. The compositions may contain a vehicle and/or a non-ionic, cationic or anionic surface active agent to ensure a uniform dispersion of the components of the composition. The vehicle may be a liquid such as water, ethanol hydrocarbons or other organic solvents or an animal, vegetable or mineral oil or a powder such as talc, clays, silicates or kieselguhr.

In practice, the stabilized compositions of the invention are preferably in the form of a wettable powder containing 5 to 90% by weight of the active metal salt or in the form of an aqueous suspension containing 10 to 70% by weight of the active metal salt. A useful form of the composition is in the form of a powder dispersible in water containing 5 to 90% by weight of the metal salt of ethylene bis dithiocarbamic acid and 0.1 to 5% by weight of cinnamic aldehyde based on the weight of the stabilized composition as well as an aqueous suspension containing 10 to 70% by weight of the metal salt of ethylene bis dithiocarbamic acid and 0.1 to 15% by weight of cinnamic aldehyde based on the weight of the stabilized composition.

The novel process of the invention for stabilizing a metal salt of ethylene bis dithiocarbamic acid or a composition containing the said salt as the active ingredient comprising incorporating at one or more steps of the synthesis or formulation of the said metal salt, a sufficient amount of cinnamic aldehyde to ensure stabilization of the salt or the composition containing the salt, the said processes being referred to hereafter as general process α. Preferably, the said salts of ethylene bis dithiocarbamic acid are the manganese or zinc salts. The process preferably uses 0.1 to 10% by weight of cinnamic aldehyde based on the weight of the stabilized metal salt or 0.1 to 20% by weight of cinnamic aldehyde based on the weight of the stabilized compositions.

The cinnamic aldehyde may be introduced at one or more of the steps for the chemical synthesis of the salt of ethylene bis dithiocarbamic acid or during the formulation of the salt to produce a fungicidal composition. In the case of maneb or zineb, the cinnamic aldehyde may be introduced either into an aqueous solution of a water soluble salt of ethylene bis dithiocarbamic acid or into aqueous solution of a water-soluble manganese or zinc salt or at the time of precipitation of the manganese or zinc salt of ethylene bis dithiocarbamic acid by simultaneous addition at the same time of the mixing of the aqueous solution of a water-soluble salt of zinc or manganese and the aqueous solution of the salt of ethylene bis dithiocarbamic acid or during the vacuum filtering of the maneb or zineb. Also, the cinnamic aldehyde may be added during the drying of maneb or zineb directly by spraying in the form of a liquid or after incorporation first into an inert solid. The incorporation of cinnamic aldehyde may take place at the time of formulation, preferably by simple mixing of liquid cinnamic aldehyde with the usual adjuvants of formulation when the composition is a liquid suspension or by mixing first the aldehyde with an inert powder to ensure a homogeneous distribution though out the components of the mixture when the composition is solid.

Included in the invention of the general process are (a) the procedure wherein cinnamic aldehyde is incorporated in one or more of the steps of the chemical synthesis of a salt of ethylene bis dithiocarbamic acid, particularly in the solution of a soluble salt of ethylene bis dithiocarbamic acid or in a solution of a soluble salt of the metal or in the suspension of the precipitate of the salt of ethylene bis dithiocarbamic acid; (b) the procedure wherein cinnamic aldehyde is added during the drying of the metal salt of ethylene bis dithiocarbamic acid by direct spraying or in the form of a powder of cinnamic aldehyde and an inert carrier; (c) the procedure used in the case in which the composition of the salt of ethylene bis dithiocarbamic acid is a liquid suspension, wherein the cinnamic aldehyde is incorporated into the mixture with the diverse formulation adjuvants; and (d) the procedure used in the case in which the composition of the salt of ethylene bis dithiocarbamic acid is a powder or a wettable powder, wherein the cinnamic aldehyde is incorporated into the final mixture after being first mixed with an inert powder to ensure a homogeneous distribution of the stabilizer through the composition.

The interest in the introduction of the stabilizer in the different steps of the chemical synthesis or the formulation of maneb or zineb is due to the fact that the presence of the stabilizer is necessary for the drying but it is also during storage of the formulated or non-formulated product before or after formulation. Now, it is known that notably when the degradation processes being combatted present a marked intensity, the introduced stabilizer is, after having played its role, more or less chemically changed. It can then be advantageous to add, after drying, another quantity of cinnamic aldehyde to ensure storage without alteration, the initial amount of stabilizer having possibly diminished notably during drying.

Moreover, it is noted that because of the type of phenomenon discussed above, the amount of cinnamic aldehyde detectable in a sample of maneb or zineb or a sample of composition containing the said products is especially much lower than the amount of stabilizer initially incorporated.

The invention equally has for its object compositions containing a metal salt of ethylene bis dithiocarbamic acid and a sufficient quantity of cinnamic aldehyde, or a compound resulting from the conversion of the said aldehyde, to stabilize the said metal salt, characterized in that they are obtained by a processes described above and especially the compositions wherein the metal salt is the manganese or zinc salt of ethylene bis dithiocarbamic acid. Also, an object of the invention is the metal salts of ethylene bis dithiocarbamic acid obtained by the above processes characterized in in that they contain a sufficient quantity of cinnamic aldehyde or a compound resulting from the conversion of the said aldehyde to ensure stabilization of the said salts and especially those wherein the metal salifiying the ethylene bis dithiocarbamic acid is manganese or zinc.

The stabilizing effect of cinnamic aldehyde is shown in comparative tests with and without addition of cinnamic aldehyde. These tests show that maneb dried at 100° C. will be stabilized against ignition by addition of cinnamic aldehyde which ignition occurs without stabilization; that the addition of cinnamic aldehyde to maneb in the form of a bulk product or in the form of a formulated product, as a wettable powder or an aqueous suspension, reduces considerably decomposition of maneb under the influence of heat and humidity; that the addition of cinnamic aldehyde to maneb greatly reduces the amount of undesired impurities such as ethylene thiourea which, without stabilization, will occur due to the influence of heat and humidity; that the addition of cinnamic aldehyde to an aqueous suspension of zineb diminishes considerably the decomposition of zineb caused by heat and humidity; that maneb and zineb obtained in the presence of cinnamic aldehyde are odorless or practically odorless and has a satisfactory color, that which is not true in the absence of the stabilizer.

The specific advantages of the stabilization process as compared to the process of the prior art are that cinnamic aldehyde is a liquid product which is easily adapted to obtain a good homogenous mixture with salts of ethylene bis dithiocarbamic acid in bulk or after formulation, the solid stabilizers, especially in the case of aqueous suspensions, having the tendency to form deposits in the bottom of their containers. Cinnamic aldehyde reduces considerably the odors caused by decomposition products of the metal salts of ethylene bis dithiocarbamic acid such as mercaptans or sulfur derivatives, and reduces in considerable fashion the formation of ethylene thiourea which tends to occur when the salts of ethylene bis dithiocarbamic acid are subjected to the influence of heat and humidity.

In the following examples there are described several preferred embodiments to illustrate the invention. However, it is to be understood that the invention is not intended to be limited to the specific embodiments.

EXAMPLE 1

STABILIZED MANEB 820 ml of an aqueous solution of ammonium ethylene bis dithiocarbamate (titer of 28.5% by weight) were added at 45° C. to 4800 ml of water and then 1,052 g of an aqueous solution of 280 g/l of magnesium sulfate were added thereto. The mixture was stirred for 30 minutes and was then vacuum filtered. The recovered precipitate was washed with water to obtain 520 g of moist maneb. The latter was intimately mixed with 8 g of cinnamic aldehyde and was then dried in open air at 100° C. to obtain 408 g of practically odorless maneb with a yellow color titrating 96% purity.

EXAMPLE 2

STABILIZED MANEB 820 ml of an aqueous solution of ammonium ethylene bis dithiocarbamate (titer of 28.5% by weight) were added at 45° C. to 4800 ml of water and then 10 g of cinnamic aldehyde and 1,052 g of an aqueous solution of 280 g/l of magnesium sulfate were simultaneously added thereto with stirring. The mixture was stored for 30 minutes and was vacuum filtered. The recovered precipitate was washed with water to obtain 532 g of moist maneb which was dried in open air at 100° C. to obtain 407 g of practically odorless, stabilized maneb with a yellow color and titrating 96% purity.

EXAMPLE 3

A aqueous suspension of maneb was prepared containing 30 g of stabilized maneb, 2 g of cinnamic aldehyde, 1 g of Brecolane N.V.A. (sodium alkyl naphthalane sulfate), 4 g of calcium lignosulfate, 0.5 g of carboxymethyl-cellulose C 300 (viscosity of 300 cp.), 10 g of ethylene glycol and 52.5 g of water.

EXAMPLE 4

A wettable powder was obtained by first mixing 3 g of cinnamic aldehyde and 3 g of silica and then admixing therewith 86.5 g of stabilized maneb, 3 g of calcium lignosulfate, 1 g of Brecolane N.V.A. and 3.5 g of silica.

EXAMPLE 5

A wettable powder was obtained by mixing 90 g of technic zineb, 2 g of cinnamic aldehyde, 3 g of calcium lignosulfate, 1 g of Brecolane N.V.A. and 4 g of silica.

EXAMPLE 6

The following tests were conducted to compare the stability of maneb with and without cinnamic aldehyde.

1. Addition of cinnamic aldehyde at the drying step 205 g of an aqueous solution of ammonium ethylene bis dithiocarbamate (titer of 28.5% by weight) were added at 45° C. to 1200 ml of water and 263 g of an aqueous solution of 280 g/l of manganese sulfate were added to the mixture. The mixture was stirred for 20 minutes and was vacuum filtered. The recovered precipitate was washed with water to obtain 130 g of moist maneb which was divided into 2 equal parts. The first part was dried in an oven in the free air at 100° C. and after a few minutes, a sudden ignition occured and the product turned black. The second part of the maneb was intimately mixed with 1 g of cinnamic aldehyde and was then dried under the same conditions as the first part to obtain 51 g of practically odorless maneb with a yellow color and a 96.5% purity. This means that the addition of cinnamic aldehyde prevents the ignition of maneb during drying in the open air at 100° C. and yields maneb with a very high degree of purity.

2. Storage of maneb with and without cinnamic aldehyde addition

The maneb was prepared as above in Example 6 and was dried at 85° C. at a pressure of 30 mm Hg to obtain 100 g of maneb which was divided into 4 equal parts. The first part was untreated and served as the control(A); the second part received 0.25 g of cinnamic aldehyde and was product (B); the third part received 0.50 g of cinnamic aldehyde and was product (C); and the fourth part received 0.75 g of cinnamic aldehyde and was product (D). 5 g of each of products A,B,C and D were placed in open receptals and were held in an over at 80° C. and 100% relative humidity. After 8 hours storage, the following results were obtained.

TABLE I

| Product | % Titer of Maneb initial | % Titer of Maneb after 8 hours | Color of Maneb initial | Color of Maneb after 8 hours |
|---|---|---|---|---|
| A | 94 | 4 | yellow | maroon/black |
| B | 93 | 60 | " | yellow |
| C | 92 | 66 | " | " |
| D | 91 | 70 | " | " |

At a temperature of 80° C. and 100% relative humidity, normal maneb titrating 94% was completely decomposed after 8 hours while samples of the same product containing cinnamic aldehyde under the same conditions contained 60 to 70% of active product after 8 hours.

3. Maneb as wettable powder with and without cinnamic aldehyde

A control wettable powder A was prepared from 85.5 g of maneb, 3 g of calcium lignosulfate, 1 g of Brecolane N.V.A. and 9.5 g of silica. Test wettable powder B was prepared from 86.5 g of maneb, 3 g of calcium lignosulfate, 1 g of Brecolane N.V.A., 7.5 g of silica and 2 g of cinnamic aldehyde and test wettable powder C was prepared from 86.5 g of maneb, 1 g of Brecolane N.V.A., 3 g of calcium lignosulfate, 6.5 g of silica and 3 g of cinnamic aldehyde. Two metal plates were suspended 19 cm and 38 cm from the floor of an oven measuring 60×60×58 cm and having a volume of 200 liters and 50 circles with 32 mm diameters were cut out of each plate and 100 crucibles of frit glass with a diameter of 30 mm of determined porosity were placed into the circles. 3 g of each lot fo products A, B and C were placed in the crucibles which were distributed at random. The oven was then adjusted to 50° C. and a relative humidity of 80% and the samples were observed at the start of the test and 10, 20 and 30 days later. The crucibles corresponding to these observations were removed from the oven, homogenized and placed in a dessiccator in the presence of phosphoric anhydride until the wieght was constant (48 hours). The titers of maneb/measured by $CS_2$ and the titer of ethylene thiourea (ETU)/was determined and the results are reported in Table II.

TABLE II

| Product | Initial $CS_2$ | Initial ETU | 10 days $CS_2$ | 10 days ETU | 20 days $CS_2$ | 20 days ETU | 30 days $CS_2$ | 30 days ETU |
|---|---|---|---|---|---|---|---|---|
| A | 83.0% | 0.25% | 25.3% | 3.9% | 5.1% | 5.9% | 3.4% | 8.3% |
| B | 83.2% | 0.18% | 70% | 0.3% | 55% | 0.8% | 49% | 1.2% |
| C | 83.0% | 0.15% | 72% | 0.3% | 61% | 0.6% | 54% | 0.9% |

The results of Table II show that at 50° C. and 80% relative humidity, a wettable powder containing maneb is practically completely decomposed in about a month and the residual product contains an amount of ethylene thiourea on the order of 8% while the wettable powders stabilized with cinnamic aldehyde still contains about 50% of active material and the amount of ethylene thiourea is only about 1% after 30 days.

4. Maneb as aqueous suspension

An aqueous suspension of maneb as prepared in Example 3 (suspension A) and an analogous suspension where the cinnamic aldehyde was replaced with water (suspension B) was stored for 6 weeks at 50° C. Suspension B was a heterogenous mass which it was impossible to use but suspension A was still homogenous and did not show a 10% loss of titer. This means that a classical aqueous suspension of maneb stored at 50° C. for 6 weeks shows a precipitation phenomenon and a hardening of the mass leading to a heterogenicity which made it impossible to use the composition while the composition with the addition of cinnamic aldehyde remained homogenous and did show only a minimum loss of titer.

EXAMPLE 7
ZINEB IN A WETTABLE POWDER 536 g of an aqueous solution of ammonium ethylene bis dithiocarbamate (titer of 28.4% by weight) were poured into 3000 ml of water and then a solution of 290 g of zinc sulfateheptahydrate in 900 ml of water was slowly added thereto. The mixture was stirred and vacuum filtered and the recovered precipitate was washed with water and dried to a constant weight at 50° C. to obtain 280 g of zineb which was divided into 2 equal parts. A wettable powder A was prepared from 90 g of zineb from the first part, 3 g of calcium lignosulfate, 1 g of Brecolane N.V.A. and 6 g of silica and a wettable powder B was prepared from 90 g of zineb from the second part, 3 g of calcium lignosulfate, 1 Brecolane N.V.A., 4 g of silica and 2 g of cinnamic aldehyde. 5 g of each of powders A and B were held in an oven at 70° C. and 100% relative humidity for 15 hours and the titer of zineb determined by measuring carbon disulfide as reported in Table III.

TABLE III

| Powder | Titer of zineb | |
|---|---|---|
| | initial | after 15 hours |
| A | 83% | 35% |
| B | 83% | 65% |

This shows that storage of a wettable powder containing zineb at 70° C. and 100% relative humidity for 15 hours resulted in a reduction of active product from 83% to 35% while the same product stabilized with cinnamic aldehyde stored under the same conditions went from 83% to 65%.

Various modifications of the products and method of the invention may be made without departing from the spirit or scope thereof and it is to be understood that the invention is intended to be limited only as defined in the appended claims.

We claim:

1. A composition comprising a metal salt of ethylene bis dithiocarbamic acid selected from the group consisting of zinc and manganese and 0.1 to 10% by weight based on the metal salt of cinnamic aldehyde to stabilize the said metal salt.

2. A composition of claim 1 in the form of a powder dispersible in water containing 5 to 90% by weight of a metal salt of ethylene bis dithiocarbamic acid selected from the group consisting of zinc and manganese and 0.1 to 5% by weight of cinnamic aldehyde based on the weight of the stabilized composition.

3. A composition of claim 1 in the form of an aqueous suspension containing 10 to 70% by weight of a metal salt of ethylene bis dithiocarbamic acid selected from the group consisting of zinc and manganese and 0.1 to 15% by weight of cinnamic aldehyde based on the weight of the stabilized composition.

4. A process for stabilizing a metal salt of ethylene bis dithiocarbamic acid selected from the group consisting of zinc and manganese or a composition containing such a salt as the active ingredient comprising introducing in at least one step of the chemical synthesis of the salt or formulation of said composition 0.1 to 10% by weight based on the metal salt of cinnamic aldehyde to ensure stabilization of the said metal salt or the composition containing it.

5. The process of claim 4 wherein the cinnamic aldehyde is incorporated during the synthesis of the metal salt.

6. The process of claim 4 wherein the cinnamic aldehyde is incorporated into an solution of a water-soluble salt of ethylene bis dithiocarbamic acid or into a solution of a water soluble salt of the metal or into a suspension of the precipitated metal salt.

7. The process of claim 4 wherein the cinnamic aldehyde is incorporated during drying of the metal salt of ethylene bis dithiocarbamic acid by direct spraying or in the form of a powder comprising cinnamic aldehyde and an inert carrier.

8. A process of claim 4 for the preparation of a composition in the form of a liquid suspension comprising incorporating cinnamic aldehyde into a mixture of diverse adjuvants for the formulation.

9. A process of claim 4 for the preparation of a composition in the form of a powder or wettable powder comprising mixing cinnamic aldehyde with an inert powder and incorporating the resulting product with the final mixture to obtain a homogenous stabilized powder or wettable powder.

* * * * *